United States Patent [19]

Wicnienski

[11] 4,350,441
[45] Sep. 21, 1982

[54] PHOTOMETRIC APPARATUS AND METHOD

[75] Inventor: Michael F. Wicnienski, Antioch, Ill.

[73] Assignee: Baxter Travenol Laboratories, Inc., Deerfield, Ill.

[21] Appl. No.: 164,357

[22] Filed: Jun. 30, 1980

[51] Int. Cl.³ .................. G01N 33/48; G01N 21/31
[52] U.S. Cl. ................ 356/40; 324/140 D; 328/161; 250/565; 356/320; 356/408; 356/434
[58] Field of Search ............. 356/40, 320, 323, 325, 356/407, 408, 434, 448; 324/140 D; 328/161; 307/358, 359, 494, 498; 250/565

[56] References Cited

U.S. PATENT DOCUMENTS

| | | | |
|---|---|---|---|
| 2,358,992 | 9/1944 | Millikan | 356/41 |
| 2,640,389 | 6/1953 | Liston | 356/41 |
| 2,722,156 | 11/1955 | Warren | 356/448 X |
| 3,522,739 | 8/1970 | Coor et al. | 356/320 |
| 3,647,299 | 3/1972 | Lavallee | 356/41 |
| 3,684,378 | 8/1972 | Lord | 356/323 |
| 3,720,813 | 3/1973 | Badessa | 356/409 X |
| 3,730,627 | 5/1973 | Kent | 356/434 X |
| 3,734,631 | 5/1973 | Justice et al. | 356/325 X |
| 3,787,124 | 1/1974 | Lowy et al. | 356/434 |
| 3,799,672 | 3/1974 | Vurek | 356/41 |
| 3,804,535 | 4/1974 | Rodriguez | 356/41 X |
| 3,952,206 | 4/1976 | Liedholz | 250/565 |
| 4,136,818 | 1/1979 | Larrabee | 233/1 R |
| 4,305,659 | 12/1981 | Bilstad et al. | 356/40 |

Primary Examiner—Vincent P. McGraw
Attorney, Agent, or Firm—Paul C. Flattery; Daniel D. Ryan; George H. Gerstman

[57] ABSTRACT

A photometric system for determining the absorbance ratio, in a sample, of two different wavelength lights. First and second lights, each having a different wavelength, are passed through the sample in alternation with each other. The radiation intensity from each light that has passed through the sample is detected. A comparator, up/down counter and digital to analog converter are coupled so that a scaling factor is derived which, when multiplied with an analog signal proportional to the intensity of the first light after it has passed through the sample, is equal to an analog signal proportional to the intensity of the second light after it has passed through the sample. The output of the counter comprises a digital word corresponding to the ratio of the absorbance ratio of the first light and the second light.

15 Claims, 2 Drawing Figures

PHOTOMETRIC APPARATUS AND METHOD

BACKGROUND OF THE INVENTION

The present invention concerns a novel photometer and method for determining the absorbance ratio, in a sample, of two lights of different wavelengths. The illustrative embodiment of the invention is directed to a spectrophotometer for determining the presence of hemoglobin in a fluid and is a modification of the photometric apparatus and method disclosed in U.S. application Ser. No. 127,732, filed Mar. 6, 1980, now U.S. Pat. No. 4,305,659.

In various applications it is necessary to detect low levels of the various hema complexes, and most particularly oxyhemoglobin and free hemoglobin in a certain fluid. For example, in systems in which plasma is collected, it is often desirable to detect the presence of low levels of hemoglobin in the collected plasma.

In one prior art type of system for detecting hemoglobin in a fluid, the loss of light traveling through the sample is detected. To this end, the operator starts the fluid flow and the output is initially set to zero. Any change in this zero output level is detected and is considered a measure of the increased level of hemolysis. One problem in connection with this prior art device is the fact that a change in turbidity might be detected as an increased level of hemolysis. Another problem is that this prior art system requires an initial zeroing procedure which must be handled properly by an operator. A further problem with respect to this prior art system is that it is subject to changes in ambient light levels.

In copending application Ser. No. 127,732, filed Mar. 6, 1980, now U.S. Pat. No. 4,305,659, a hemolysis detector is disclosed which determines the red/green absorbance ratio of the sample. In this manner, the presence of even small traces of hemoglobin can be detected in a fluid, such as plasma. In the copending application, intensity leveling of the two light sources is required. The present invention obviates the need for such intensity leveling by utilizing a direct division of the light outputs. Further, by utilizing the present invention the output of the system may be in the form of a digital word, thereby enabling efficient and inexpensive display of the result in a digital form. Another advantage of the present invention is that the absolute magnitude of the signals produced by the light sources is relatively unimportant, so long as the relative ratio of the light source outputs tends to remain constant.

It is, therefore, an object of the present invention to provide an apparatus and method for determining the absorbance, in a sample, of two different wavelength lights.

Another object of the present invention is to provide a hemolysis detector which operates to detect hemoglobin in a fluid by determining the red/green absorbance ratio of the fluid.

Another object of the present invention is to provide a system for determining the color of a sample by using known absorbance characteristics and passing two colors through the sample and then determining the ratio of absorbance of the two colors.

A still further object of the present invention is to provide apparatus and a method for determining the color absorbance ratio of a fluid with the apparatus and method being blind to ambient light level changes.

A further object of the present invention is to provide an apparatus for determining the color absorbance ratio of a sample, with the apparatus being relatively simple in construction and easy to manufacture.

Another object of the present invention is to provide a system for determining the color absorbance ratio of a sample, without requiring intensity leveling of the light sources.

A further object of the present invention is to provide a system for determining the color absorbance ratio of a sample, and for enabling the display of the results in a digital form without requiring complex digital circuitry.

Other objects and advantages of the invention will become apparent as the description proceeds.

SUMMARY OF THE INVENTION

In accordance with the present invention, a system is provided for determining the absorbance ratio in a sample of two different wavelength lights. The system comprises a first light having a first wavelength and a second light having a second wavelength. The first and second lights are provided in alternation with each other and the radiation intensity from each light is detected after it has passed through the sample. A scaling factor is derived which, when multiplied with an analog signal that is proportional to the intensity of the second light after it has passed through the sample, is equal to an analog signal that is proportional to the intensity of the first light after it has passed through the sample.

In the illustrative embodiment, a comparator is provided having two inputs and an output. A digital to analog converter is provided having two inputs and an output. An up/down counter is provided having an up/down input and an output. The output of the digital to analog converter is coupled to an input of the comparator while the other input of the comparator receives a signal that is proportional to the detected intensity from the first light. A signal that is proportional to the detected intensity from the second light is fed to an input of the digital to analog converter while the output of the up/down counter is coupled to the other input of the digital to analog converter. The output of the comparator is coupled to the input of the counter and means are provided for clocking the up/down counter.

In the illustrative embodiment, the first light is green and the second light is red. The comparator operates to compare the first analog signal that is proportional to the intensity of the first light with (a) a second analog signal that is proportional to the intensity of the second light times (b) a scaling factor that when multiplied with the second analog signal is equal to the first analog signal.

A more detailed explanation of the invention is provided in the following description and claims, and is illustrated in the accompanying drawings.

DETAILED DESCRIPTION OF THE ILLUSTRATIVE EMBODIMENT

Figure 1:
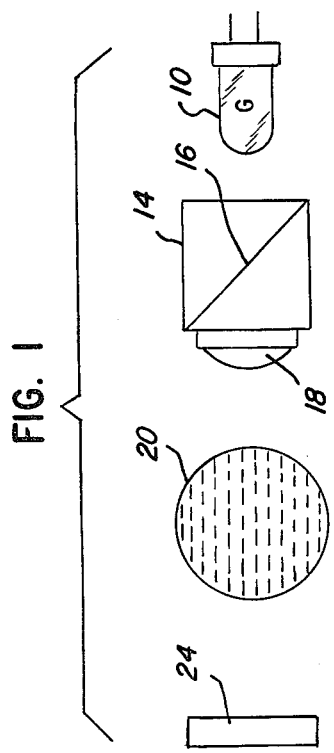
FIG. 1 is a diagram of a photometer system constructed in accordance with the principles of the present invention.

Referring to FIG. 1, a photometer apparatus is shown therein comprising a first source of light 10 having a first wavelength, a second source of light 12 having a second wavelength, a cube beam splitter 14 having a mirror 16 which preferably reflects 50 percent of the light impinging upon it and transmits 50 percent of the light through the mirror, a collimating lens 18 for directing light from the beam splitter 14 through a sample 20, and a photodetector 24. It should be understood that the reflection-transmission ratio of mirror 16 may be other than 50:50.

In the illustrative embodiment, the photometer system is used to detect hemoglobin in plasma that is being collected. Thus sample 20 comprises the plasma and it has been found satisfactory to provide light source 10 in the form of a green light emitting diode (LED) having a peak wavelength of 565 nm, and light source 12 in the form of a red LED having a peak wavelength of 635 nm.

Green light 10 and red light 12 are perpendicularly located with respect to each other and with respect to beam splitter 14. Photodetector 24 is positioned opposite beam splitter 14 from green light 10, with the sample 20 interposed between photodetector 24 and beam splitter 14. Collimating lens 18 operates to direct the light from beam splitter 14 through the sample and to photodetector 24. It can be seen that the photodetector 24 receives the absorbed radiation after the light has passed through sample 20.

In order to determine the green/red absorbance ratio of the plasma 20, the green light from LED 10 and the red light from LED 12 are directed through plasma 20 in alternation, and the respective intensities of the green and red lights after they have passed through the plasma 20 are detected by photodetector 24. A scaling factor is derived which, when multiplied with a signal that is proportional to the intensity of the red light after it has passed through the plasma 20, is equal to a signal that is proportional to the intensity of the green light after it has passed through the plasma 20. This scaling factor comprises the ratio of the absorbance of the green light and the red light.

Figure 2:
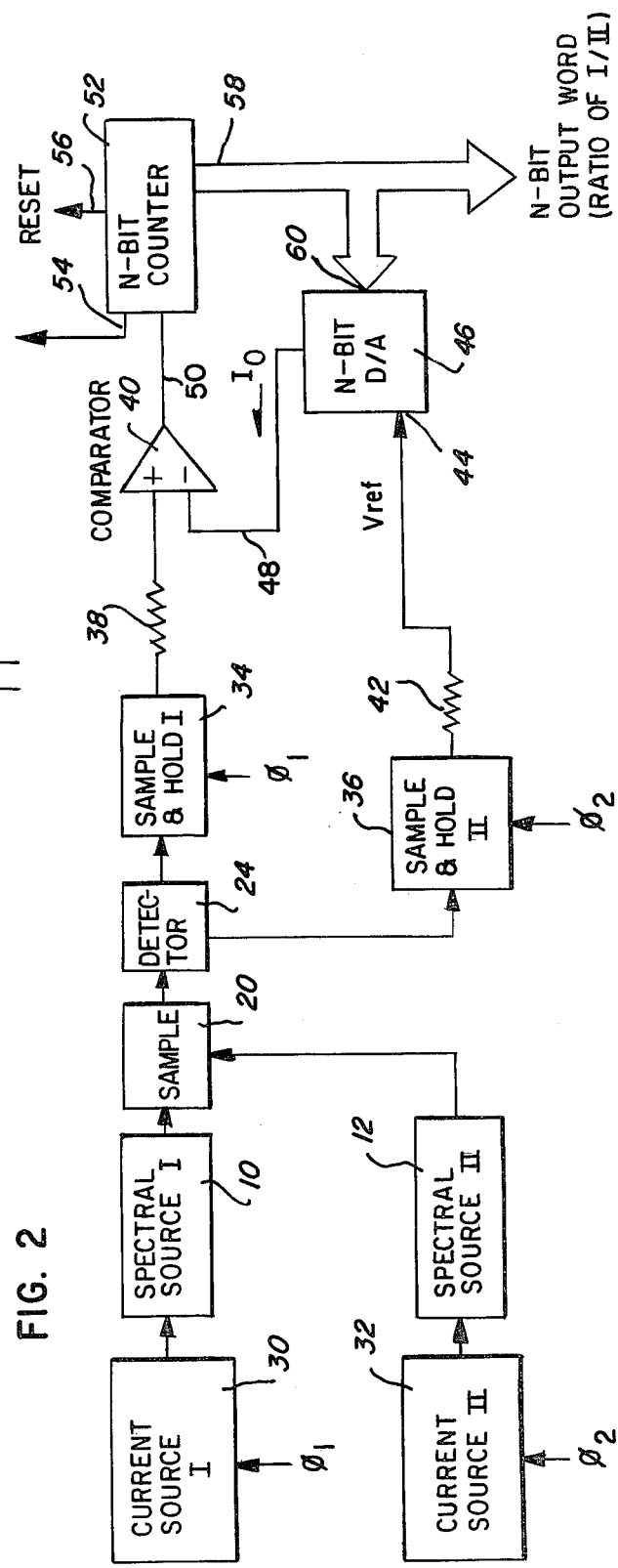
FIG. 2 is a schematic circuit diagram of a control circuit for the photometer system of FIG. 1.

The control circuit for achieving the above objectives is illustrated in FIG. 2. Referring now to FIG. 2, a current source 30 providing a square wave having a first phase is used to drive green LED 10 while a current source 32 providing a square wave which is 180° out of phase with the square wave of current source 30 is used to drive red LED 12. In this manner, green LED 10 and red LED 12 will be energized in alternation.

The lights emitted in alternation by LED 10 and LED 12 are passed through sample 20 and detected by photodetector 24. A sample and hold circuit, in a conventional form as is well-known in the art, is utilized as a demodulator to convert the alternating nature of the detector information into a continuous voltage representing the transmitted intensity of the light. Thus sample and hold circuit 34 converts the detected green light information and provides an output voltage representing an analog that is proportional to the intensity of the green light received by detector 24. Likewise, sample and hold circuit 36 provides an analog voltage output that is proportional to the detected intensity of the red light. The voltage at the output of sample and hold circuit 34 is presented to a resistor 38 so that a current at the positive input of a comparator 40 will be in proportion to the detected intensity of the green light.

The voltage at the output of sample and hold circuit 36 is presented to resistor 42 so that a current that is proportional to the detected intensity of the red light will be fed to input 44 of N-bit digital to analog converter 46. The output of digital to analog converter 46 is fed via line 48 to the negative input of comparator 40. The output of comparator 40 is fed via line 50 to the up/down input of an N-bit counter 52 having a clock input 54, a reset input 56, and an output 58. The output of N-bit counter 52 is in the form of an N-bit output word that is fed to other input 60 of the digital to analog converter 46.

The output of the digital to analog converter on line 48 comprises a current that is equal to the analog signal at input 44 times the output digital word from counter 52 which is at input 60. As stated above, that output current on line 48 is fed to a negative input of comparator 40. When the positive input of comparator 40 is higher than the negative input of comparator 40, counter 52, which is being clocked, will continue to count up until the negative input of the comparator 40 is equal to the positive input of the comparator. At that time, the comparator output will shift and counter 52 will start counting down until there is a balance. The balance is essentially the output word which comprises the ratio of the green intensity to the red intensity.

Thus the combination of the comparator 40, counter 52 and digital to analog converter 46 are coupled to derive a scaling factor (which is the output of counter 52) which, when multiplied with the analog signal at input 44, is equal to the analog signal at the positive input to comparator 40. It can be seen that the absolute magnitude of the currents produced by LEDs 10 and 12 is not significant so long as the relative ratio of the outputs of LEDs 10 and 12 remain constant.

It is desirable that the clock frequency at input 54 of counter 52 be higher than the frequency of the square waves from current sources 30 and 32, by a factor of at least 5N, where N is the bit-resolution desired. In the illustrative embodiment, counter 52 is clocked at a rate of 1 kilohertz.

Although there is no limitation intended with respect thereto, as an illustrative example comparator 40 could comprise a Motorola MLM311 comparator, digital to analog converter 46 could comprise a Motorola MC1408L8 D/A converter, and counter 52 could comprise a pair of cascaded RCA CD4029AE counters.

Although an illustrative embodiment of the invention has been shown and described, it is to be understood that various modifications and substitutions may be made by those skilled in the art without departing from the novel spirit and scope of the present invention.

What is claimed is:

1. A photometric apparatus for determining the absorbance ratio in a sample of two different wavelength lights, said apparatus comprising:
    means for providing a light of a first wavelength having, when said light is energized, a postsample intensity after said light is directed through the sample;
    means for providing a light of a second wavelength having, when said light is energized, a postsample intensity after said light is directed through the sample;
    means for alternately energizing said first and second lights;
    means for detecting said postsample intensities of said first and second lights;
    a comparator having two inputs and an output;
    a digital to analog converter having two inputs and an output;
    means coupling the output of said digital to analog converter to an input of said comparator;

means coupled to the other input of said comparator for providing a signal that is proportional to said detected postsample intensity of said first light;

means coupled to an input of said digital to analog converter for providing a signal that is proportional to said detected postsample intensity of said second light;

an up/down counter having an up/down input and an output;

means coupling the output of the comparator to the up/down input of said counter;

means coupling the output of the up/down counter to the other input of said digital to analog converter; and means for clocking said up/down counter.

2. An apparatus according to claim 1, and further including a first sample and hold circuit coupled between said detector means and said other input of said comparator; and a second sample and hold circuit coupled between said detector means and said first mentioned input of said digital to analog converter.

3. An apparatus according to claim 1, wherein said first light is green and said second light is red.

4. An apparatus according to claim 1
and further including a beam splitter positioned adjacent said first and second lights, with each of said first and second lights being directed substantially perpendicularly with respect to each other, and a holder for holding the sample, and wherein said detecting means includes photodetector means positioned such that said sample holder is located between said photodetector means and said beam splitter, said photodetector means being operative for detecting said postsample intensities of said first and second lights.

5. A photometric apparatus for determining the absorbance ratio in a sample of two different wavelength lights, said apparatus comprising:

means for providing a light of a first wavelength having, when said light is energized, a postsample intensity after said light is directed through the sample;

means for providing a light of a second wavelength having, when said light is energized, a postsample intensity after said light is directed through the sample;

means for alternately energizing said first and second lights;

means for detecting said postsample intensities of said first and second lights; and means for generating a first analog signal that is proportional to said postsample intensity of said first light;

means for comparing said first analog signal with an other signal and for generating a succession of scaling factors which
incrementally increase in value if said first analog signal is greater than said other signal,
incrementally decrease in value if said first analog signal is less than said other signal, and
remain constant in value if said first analog signal is equal to said other signal, means for generating a second analog signal that is proportional to said postsample intensity of said second light; and means operatively connected with said second analog signal generating means and said comparing means for generating a succession of said other signals by multiplying said second analog signal with each of said successive scaling factors and for transmitting said succession of said other signals to said comparing means, whereby said scaling factor, once constant, comprises the ratio of the absorbance of said first light and said second light.

6. An apparatus according to claim 5
wherein said comparing means comprises a comparator having two inputs, one of which is operatively connected with said first analog signal generating means, and an output, an up/down counter for generating at its output said scaling factors, and means for coupling the output of said comparator to the up/down input of said counter, and wherein said other signal generating means includes a digital to analog converter having one input operatively connected with said second analog signal generating means, another input operatively connected with said output of said up/down counter, and an output operatively connected with said second input of said comparing means.

7. A method for determining the absorbance ratio in a sample of two different wavelength lights, which comprises the steps of:

energizing a first light having a first wavelength;

alternately energizing a second light having a second wavelength;

directing the first light and the second light through the sample and detecting the radiation intensity of each light after it has passed through the sample;

generating a first analog signal that is proportional to the intensity of the first light after it has passed through the sample;

comparing the first analog signal with an other signal and then generating a succession of scaling factors which
incrementally increase in value if the first analog signal is greater than the other signal,
incrementally decrease in value if the first analog signal is less than the other signal, and
remain constant in value if the first analog signal is equal to the other signal, generating a second analog signal that is proportional to the intensity of the second light after it has passed through the sample, and generating a succession of the other signals by multiplying the second analog signal with each of the successive scaling factors, whereby the scaling factor, once constant, comprises the ratio of the absorbance of the first light and the second light.

8. A method for determining the absorbance ratio in a sample of two different wavelength lights, which comprises the steps of:

energizing a first light having a first wavelength;

alternately energizing a second light having a second wavelength;

directing the first and second lights through the sample and detecting the radiation intensity from each light after it has passed through the sample;

providing to a comparator a signal that is proportional to the detected intensity from said first light;

providing to a digital to analog converter a signal that is proportional to the detected intensity from said second light;

coupling the output of said comparator to the up/down input of an up/down counter;

coupling the output of said up/down counter to another input of the digital to analog converter; and
coupling the output of the digital to analog converter to the other input of said comparator.

9. An apparatus for detecting the presence of hemoglobin in a fluid which comprises
  means for providing a substantially green light having, when said light is energized, a postsample intensity after said light is directed through the sample;
  means for providing a substantially red light having, when said light is energized, a postsample intensity after said light is directed through the sample;
  means for alternately energizing said green and red lights;
  means for detecting said postsample intensities of said green and red lights;
  a comparator having two inputs and an output;
  a digital to analog converter having two inputs and an output;
  means coupling the output of said digital to analog converter to an input of said comparator;
  means coupled to the other input of said comparator for providing a signal that is proportional to said detected postsample intensity of said green light;
  means coupled to an input of said digital to analog converter for providing a signal that is proportional to said detected postsample intensity of said red light;
  an up/down counter having an up/down input and an output;
  means coupling the output of the comparator to the up/down input of said counter;
  means coupling the output of the up/down counter to the other input of said digital to analog converter; and
  means for clocking said up/down counter.

10. An apparatus according to claim 9, and further including a first sample and hold circuit coupled between said detector means and said other input of said comparator; and a second sample and hold circuit coupled between said detector means and said first mentioned input of said digital to analog converter.

11. An apparatus according to claim 9
  and further including a beam splitter positioned adjacent said green and red lights, with each of said green and red lights being directed substantially perpendicularly with respect to each other, and a holder for holding the sample, and
  wherein said detecting means includes photodetector means positioned such that said sample holder is located between said photodetector means and said beam splitter, said photodetector means being operative for detecting said postsample intensities of said green and red lights.

12. An apparatus for detecting the presence of hemoglobin in a fluid which comprises
  means for providing a substantially green light having, when said light is energized, a postsample intensity after said light is directed through the sample;
  means for providing a substantially red light having, when said light is energized, a postsample intensity after said light is directed through the sample;
  means for alternately energizing said green and red lights;
  means for detecting said postsample intensities of said green and red lights;
  means for generating a first analog signal that is proportional to said postsample intensity of said green light;
  means for comparing said first analog signal with an other signal and for generating a succession of scaling factors which
    incrementally increase in value if said first analog signal is greater than said other signal,
    incrementally decrease in value if said first analog signal is less than said other signal, and
    remain constant in value if said first analog signal is equal to said other signal,
  means for generating a second analog signal that is proportional to said postsample intensity of said red light; and
  means operatively connected with said second analog signal generating means and said comparing means for generating a succession of said other signals by multiplying said second analog signal with said successive scaling factors and for transmitting said succession of said other signals to said comparing means,
  whereby said scaling factor, once constant, comprises the ratio of the absorbance of said first green and said red light.

13. An apparatus according to claim 12
  wherein said comparing means comprises a comparator having two inputs, one of which is operatively connected with said first analog signal generating means, and an output, and
  wherein said other signal generating means includes a digital to analog converter having one input operatively connected with said second analog signal generating means, another input operatively connected with said output of said up/down counter, and an output operatively connected with said second input of said comparing means.

14. A method for detecting hemoglobin in a fluid which comprises the steps of:
  energizing a substantially green light;
  alternately energizing a substantially red light;
  directing the green light and the red light through the sample and detecting the radiation intensity of each light after it has passed through the sample;
  generating a first analog signal that is proportional to the intensity of the first light after it has passed through the sample;
  comparing the first analog signal with an other signal and then generating a succession of scaling factors which
    incrementally increase in value if the first analog signal is greater than the other signal,
    incrementally decrease in value if the first analog signal is less than the other signal, and
    remain constant in value if the first analog signal is equal to the other signal,
  generating a second analog signal that is proportional to the intensity of the second light after it has passed through the sample, and
  generating a succession of the other signals by multiplying the second analog signal with the successive scaling factors,
  whereby the scaling factor, once constant, comprises the ratio of the absorbance of the green light and the red light.

15. A method for detecting hemoglobin in a fluid which comprises the steps of:
  energizing a substantially green light;

alternately energizing a substantially red light;
directing the green and red lights through the sample and detecting the radiation intensity from each light after it has passed through the sample;
providing to a comparator a signal that is proportional to the detected intensity from said green light;
providing to a digital to analog converter a signal that is proportional to the detected intensity from said red light;
coupling the output of said comparator to the up-/down input of an up/down counter;
coupling the output of said up/down counter to another input of the digital to analog converter; and
coupling the output of the digital to analog converter to the other input of said comparator.

* * * * *